United States Patent
Kobayashi

(10) Patent No.: US 11,571,109 B2
(45) Date of Patent: Feb. 7, 2023

(54) MEDICAL OBSERVATION DEVICE

(71) Applicant: Sony Olympus Medical Solutions Inc., Tokyo (JP)

(72) Inventor: Motoaki Kobayashi, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/633,158

(22) PCT Filed: Jul. 31, 2018

(86) PCT No.: PCT/JP2018/028736
§ 371 (c)(1),
(2) Date: Jan. 23, 2020

(87) PCT Pub. No.: WO2019/026929
PCT Pub. Date: Feb. 7, 2019

(65) Prior Publication Data
US 2021/0153719 A1      May 27, 2021

(30) Foreign Application Priority Data

Aug. 3, 2017   (JP) .............................. JP2017-151055

(51) Int. Cl.
*A61B 1/00*      (2006.01)
(52) U.S. Cl.
CPC ...... *A61B 1/00009* (2013.01); *A61B 1/00013* (2013.01); *A61B 1/00045* (2013.01); *A61B 1/00188* (2013.01); *A61B 1/00193* (2013.01)
(58) Field of Classification Search
CPC ............ A61B 1/00009; A61B 1/00013; A61B 1/00045; A61B 1/00188; A61B 1/00193;
(Continued)

(56) References Cited

U.S. PATENT DOCUMENTS 5,577,991 A  *  11/1996  Akui ................... A61B 1/0005
                                                         600/111
2004/0173914 A1    9/2004  Kurihara et al.
(Continued)

FOREIGN PATENT DOCUMENTS

CN         104185441 A     12/2014
CN         106028903 A     10/2016
(Continued)

OTHER PUBLICATIONS

International Search Report and Written Opinion dated Oct. 23, 2018 for PCT/JP2018/028736 filed on Jul. 31, 2018, 8 pages including English Translation of the International Search Report.
(Continued)

*Primary Examiner* — Timothy J Neal
*Assistant Examiner* — Sung Ham
(74) *Attorney, Agent, or Firm* — Xsensus LLP

(57) ABSTRACT

A medical observation device according to the present invention includes: an imaging unit that capture an image of a subject at a first angle of view; and an image generating unit that generates a display image signal by cutting, at a second angle of view smaller than the first angle of view, the image captured by the imaging unit at the first angle of view, and performing image processing thereon. This medical observation device enables the hand-eye coordination and definition to be maintained even if the field of view is changed.

20 Claims, 8 Drawing Sheets

(58) Field of Classification Search
CPC ........... A61B 1/0005; A61B 1/04; A61B 1/06; H04N 5/3572; H04N 2005/2255; H04N 5/23277
USPC ..................... 348/208.5, 5.046; 600/109, 921
See application file for complete search history.

(56) References Cited

U.S. PATENT DOCUMENTS

| | | | |
|---|---|---|---|
| 2010/0026835 A1* | 2/2010 | Negishi | H04N 9/643 348/223.1 |
| 2011/0018969 A1* | 1/2011 | Tanaka | H04N 5/23296 348/47 |
| 2011/0057930 A1* | 3/2011 | Keller | G06T 7/521 345/419 |
| 2011/0228049 A1* | 9/2011 | Kazakevich | H04N 13/128 348/45 |
| 2012/0048607 A1 | 3/2012 | Takahashi et al. | |
| 2013/0342641 A1* | 12/2013 | Morioka | G03B 35/08 348/36 |
| 2014/0307072 A1 | 10/2014 | Takahashi | |
| 2014/0350338 A1* | 11/2014 | Tanaka | A61B 1/00193 600/111 |
| 2014/0375781 A1* | 12/2014 | Ono | A61B 1/05 348/61 |
| 2015/0018618 A1* | 1/2015 | Ikeda | A61B 1/00193 600/111 |
| 2015/0156461 A1 | 6/2015 | Jessop et al. | |
| 2016/0259159 A1* | 9/2016 | Matsui | G02B 23/26 |
| 2016/0353968 A1 | 12/2016 | Ikuma et al. | |
| 2017/0111624 A1 | 4/2017 | Jingu et al. | |
| 2017/0172392 A1* | 6/2017 | Ito | A61B 1/05 |
| 2017/0251911 A1* | 9/2017 | Ito | G02B 23/2438 |
| 2018/0262736 A1* | 9/2018 | Amano | A61B 1/00188 |

FOREIGN PATENT DOCUMENTS

| | | |
|---|---|---|
| CN | 106999024 A | 8/2017 |
| JP | 5-211202 A | 8/1993 |
| JP | 08-160316 A | 6/1996 |
| JP | 2004-327951 A | 11/2004 |
| JP | 2012-016406 A | 1/2012 |
| JP | 2012-49219 A | 3/2012 |
| JP | 2015-005896 A | 1/2015 |
| JP | 2019-029876 A | 2/2019 |
| WO | 2017/038774 A1 | 9/2017 |
| WO | 2017/169014 A1 | 10/2017 |

OTHER PUBLICATIONS

Japanese Office Action dated Jun. 2, 2020, issued in corresponding Japanese Patent Application No. 2015-248860.
European Office Action dated Jun. 8, 2020, issued in corresponding European Patent Application No. 18841890.9.

* cited by examiner

MEDICAL OBSERVATION DEVICE

CROSS-REFERENCE TO RELATED APPLICATIONS

The present application is based on PCT filing PCT/JP2018/028736, filed Jul. 31, 2018, which claims priority to JP 2017-151055, filed Aug. 3, 2017, the entire contents of each are incorporated herein by reference.

TECHNICAL FIELD

The present invention relates to medical observation devices.

BACKGROUND ART

Demand for stereoscopic observation in medical endoscope systems has been increasing. Various systems have been conventionally known as stereoscopic endoscope systems. For example, disclosed in Patent Literature 1 is a stereoscopic endoscope system including: a rigid endoscope having a primary optical system; a secondary optical system that splits light condensed by the primary optical system; and two imaging elements that respectively captures a left-eye image signal and a right-eye image signal, based on light split by the secondary optical system. Used according to Patent Literature 1 is a pupil splitting method, in which two reflecting mirrors serving as the secondary optical system are arranged at pupil positions of the primary optical system, and a beam of light taken in by the primary optical system is split. In this pupil splitting method, by change in the interval between the two reflecting mirrors, the three-dimensionality in the depth direction is changed. However, in the pupil splitting method, when the parallax is increased, the quantity of light passing through the optical path is decreased, and thus the more the parallax is increased, the more the definition is reduced.

A twin-lens relay system, in which a rigid endoscope has an optical system for the left eye and an optical system for the right eye, has also been known as a system enabling reduction in the definition to be made small even if the parallax is increased. In the twin-lens relay system, since each of light for the left eye and light for the right eye is able to be independently taken in, reduction in the definition upon increase in the parallax is able to be made small.

CITATION LIST

Patent Literature

Patent Literature 1: Japanese Patent Application Laid-open No. H08-160316

DISCLOSURE OF INVENTION

Technical Problem

When a rigid endoscope is rotated about an axis parallel to the optical axis as the rigid endoscope is moved for change in the field of view, the image displayed on a monitor or the like is also rotated. In the twin-lens relay system, in association with the rotation of the image due to the rotation of the rigid endoscope, the top and bottom relation on the monitor and the actual top and bottom relation do not match on the display screen. Due to this mismatch between the top and bottom relation on the monitor and the actual top and bottom relation, coordination between the eye and hand, the so-called hand-eye coordination, is not retained.

The present invention has been made in view of the above, and an object thereof is to provide a medical observation device that enables the hand-eye coordination and the definition to be maintained even if the field of view is changed.

Solution to Problem

To solve the above-described problem and achieve the object, a medical observation device according to the present invention includes: an imaging unit configured to capture an image of a subject, at a first angle of view; and an image generating unit configured to generate a display image signal by cutting, at a second angle of view smaller than the first angle of view, the image captured by the imaging unit at the first angle of view, and performing image processing thereon.

Moreover, in the above-described medical observation device according to the present invention, the imaging unit includes: a first imaging unit configured to capture an image of a subject at the first angle of view; and a second imaging unit configured to capture an image of the subject at the first angle of view, the image having a field of view different from that of the image captured by the first imaging unit, and the image generating unit is configured to cut out images, for the first angle of view for the first imaging unit and the first angle of view for the second imaging unit, at the second angle of view, at positions corresponding to each other, and generate a parallax image based on the cut-out images.

Moreover, the above-described medical observation device according to the present invention further includes: an input unit configured to receive input of operation for a cut-out position in the image at the first angle of view, wherein the image generating unit is configured to cut, at the second angle of view, the image at the first angle of view, at a position corresponding to the input of the operation received by the input unit.

Moreover, in the above-described medical observation device according to the present invention, the image generating unit is configured to perform upconversion and generate the display image signal, after cutting, at the second angle of view, the image at the first angle of view.

Advantageous Effects of Invention

The present invention has an effect of enabling the hand-eye coordination and the definition to be maintained even if the field of view is changed.

BEST MODE FOR CARRYING OUT THE INVENTION

Figure 1:
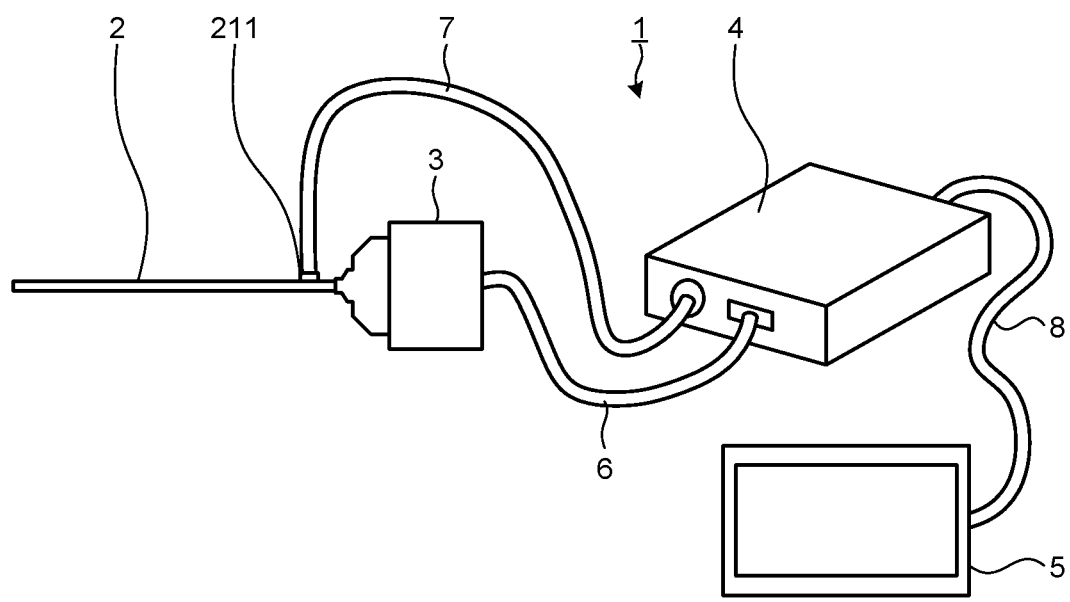
FIG. 1 is a diagram illustrating a schematic configuration of a medical endoscope system according to an embodiment of the present invention.

Described hereinafter are modes for carrying out the present invention (hereinafter, referred to as "embodiments"). With respect to the embodiments, medical endoscope systems for capturing and displaying in-vivo images of subjects, such as patients, will be described as examples of an endoscope apparatus according to the present invention. Furthermore, the present invention is not limited to these embodiments. Moreover, in the description, the same portions in the drawings will be assigned with the same reference signs throughout the drawings.

EMBODIMENTS

FIG. 1 is a diagram illustrating a schematic configuration of a medical endoscope system 1 according to an embodiment of the present invention. The medical endoscope system 1 illustrated in FIG. 1 is a system for stereoscopic observation of the interior of a living body. The medical endoscope system 1 includes: a rigid endoscope 2 having a distal end portion that is inserted into the living body, condenses light in the living body, and illuminates the living body; a camera head 3 that images light from the living body, the light having been condensed by the rigid endoscope 2, and generates two image signals having a parallax from each other; a control device 4 that controls operation of the camera head 3, and generates illumination light to be supplied to the rigid endoscope 2; a display device 5 that is connected to the control device 4 and displays information, such as an image; a transmission cable 6 that connects the camera head 3 and the control device 4 to each other, and transmits an electrical signal or the like therethrough; a light guide cable 7 that connects the rigid endoscope 2 and the control device 4 to each other and transmits illumination light therethrough; and a video cable 8 that connects the control device 4 and the display device 5 to each other, and transmits information, such as an image, therethrough. The rigid endoscope 2 and the camera head 3 form an imaging device 101.

Figure 2:
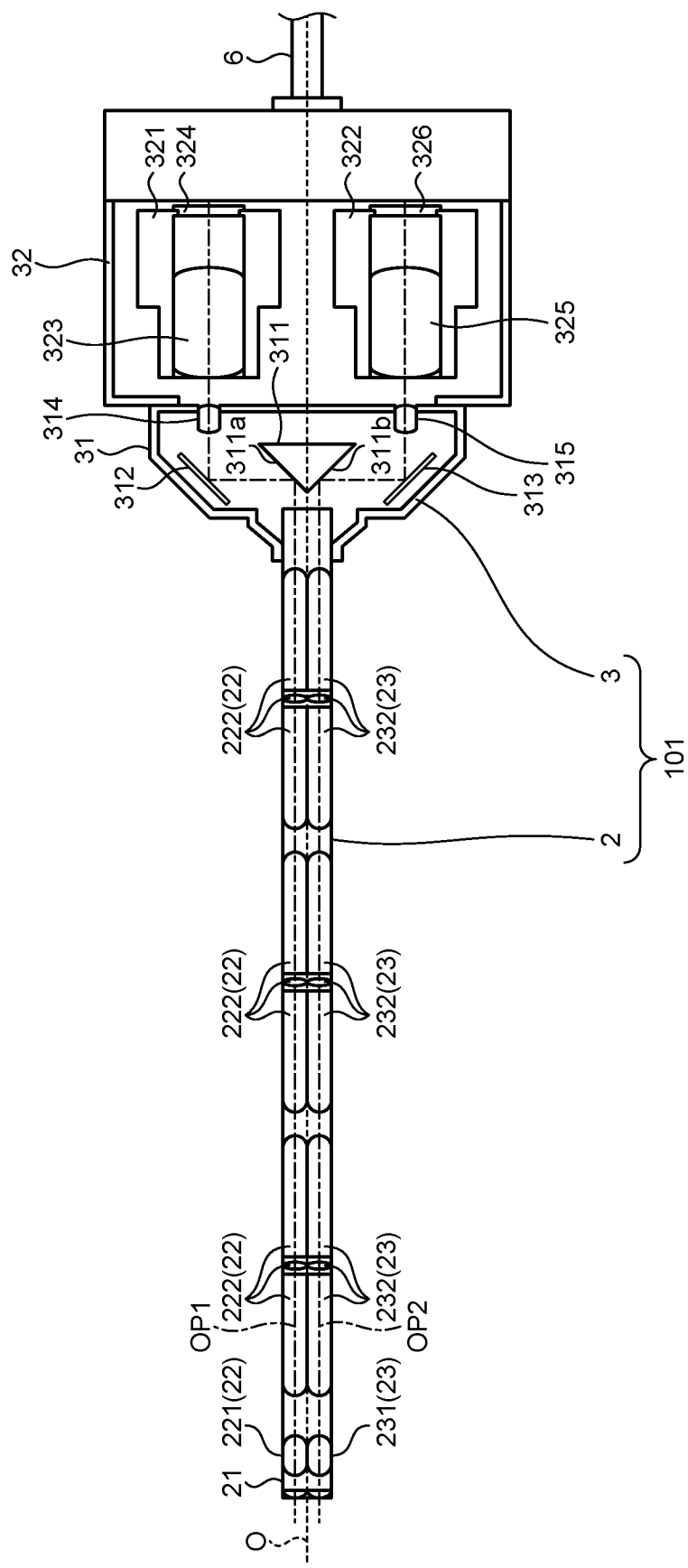
FIG. 2 is a diagram illustrating an internal configuration of a rigid endoscope and a camera head both included in the medical endoscope system according to the embodiment of the present invention.

FIG. 2 is a diagram illustrating an internal configuration of the rigid endoscope 2 and camera head 3. FIG. 2 is a diagram where the rigid endoscope 2 and the camera head 3 both illustrated in FIG. 1 have been rotated by 90°, with a longitudinal axis thereof being a rotation axis.

Firstly described is a configuration of the rigid endoscope 2. The rigid endoscope 2 has: an insertion tube 21 that is rigid and elongated; and a first condensing optical system 22 and a second condensing optical system 23 that are installed side by side inside the insertion tube 21. Furthermore, the rigid endoscope 2 is provided with an illumination optical system, which propagates therethrough illumination light from a light source that the control device 4 has, and irradiates the living body with the illumination light. The rigid endoscope 2 is detachably and unrotatably connected to the camera head 3.

An outer peripheral portion of the insertion tube 21 is provided with an attachment portion 211, to which a distal end portion of the light guide cable 7 is attached. The attachment portion 211 extends in a direction orthogonal to the central axis O of the insertion tube 21. The attachment portion 211 is connected to the illumination optical system inside the insertion tube 21. The illumination optical system guides light input from the attachment portion 211, to a distal end of the insertion tube 21, and outputs the light to the exterior of the insertion tube 21. The attachment portion 211 is also called a light guide post.

The first condensing optical system 22 has, in order from a distal end portion side of the insertion tube 21, a first objective optical system 221 and a first relay optical system 222. The first objective optical system 221 is provided in a distal end portion of the insertion tube 21, and condenses first observation light from an observed region inside the living body. The first relay optical system 222 guides the first observation light condensed by the first objective optical system 221, to a proximal end (a right end portion in FIG. 2) of the insertion tube 21. The first observation light is output from the proximal end of the insertion tube 21 to the camera head 3.

Similarly to the first condensing optical system 22, the second condensing optical system 23 has, in order from a distal end side thereof, a second objective optical system 231 and a second relay optical system 232. Second observation light condensed by the second condensing optical system 23 is output from the proximal end of the insertion tube 21 to the camera head 3. Inside the insertion tube 21, the second condensing optical system 23 is separate from the first condensing optical system 22 in a radial direction of the insertion tube 21. An optical axis OP2 of the second condensing optical system 23 is at a position symmetric to an optical axis OP1 of the first condensing optical system 22, with respect to the central axis O of the insertion tube 21. The second condensing optical system 23 has a parallax, but the size of the image circle and the focal position of the second condensing optical system 23 are the same as those of the first condensing optical system 22.

Described next is a configuration of the camera head 3 by reference to FIG. 2. The camera head 3 has: an optical path separating unit 31 that separates an optical path of the first observation light from the first condensing optical system 22 and an optical path of the second observation light from the second condensing optical system 23, from each other; and an imaging unit 32 that images each of the first observation light and second observation light, and generates two image signals.

The optical path separating unit 31 has: a triangular prism 311 that reflects each of the first observation light and second observation light and changes optical paths of the first observation light and second observation light into directions opposite to each other; a pair of mirrors 312 and 313 that respectively reflect the first observation light and second observation light reflected by the triangular prism 311 such that their optical paths are made parallel to each other; and a pair of eyepiece optical systems 314 and 315 that respectively output the first observation light and second observation light respectively reflected by the mirrors 312 and 313, to the imaging unit 32.

The triangular prism 311 has a triangular prism shape having a bottom surface with a rectangular equilateral triangle shape, and has a first side surface 311a and a second side surface 311b, which have areas equal to each other, are orthogonal to each other, and are respectively arranged at 45 degrees from the optical axis OP1 of the first condensing optical system 22 and the optical axis OP2 of the second condensing optical system 23, in the rigid endoscope 2 attached to the camera head 3. The first side surface 311a reflects the first observation light upward in FIG. 2 by bending its optical path by 90 degrees. The second side surface 311b reflects the second observation light downward in FIG. 2 by bending its optical path by 90 degrees.

The mirror 312 and mirror 313 are positioned at symmetrical positions with respect to the central axis O of the insertion tube 21 of the rigid endoscope 2 connected to the camera head 3. A surface of the mirror 312 has an angle of 45 degrees with respect to a direction, in which the first observation light reflected by the first side surface 311a comes, and reflects the first observation light in a direction parallel to the central axis O. A surface of the mirror 313 has an angle of 45 degrees with respect to a direction, in which the second observation light reflected by the second side surface 311b comes, and reflects the second observation light in a direction parallel to the central axis O.

The eyepiece optical system 314 and eyepiece optical system 315 are at symmetrical positions with respect to the central axis O of the insertion tube 21. The first observation light reflected by the mirror 312 goes into the imaging unit 32 through the eyepiece optical system 314. Furthermore, the second observation light reflected by the mirror 313 goes into the imaging unit 32 through the eyepiece optical system 315.

The imaging unit 32 has: a first imaging unit 321 that images the first observation light and generates an image signal (a right-eye image signal); and a second imaging unit 322 that images the second observation light and generates an image signal (a left-eye image signal).

The first imaging unit 321 has: a first imaging optical system 323 that condenses the first observation light output from the eyepiece optical system 314; and a first imaging element 324 that photoelectrically converts the first observation light condensed by the first imaging optical system 323, and generates the right-eye image signal. The first imaging optical system 323 has: an optical zooming mechanism (not illustrated in the drawings), which is formed by use of one or plural lenses movable along the optical axis OP1, and changes the angle of view under control by the control device 4; and a focusing mechanism (not illustrated in the drawings) that changes the focus. The first imaging element 324 is formed by use of an image sensor, such as a charge coupled device (CCD), a complementary metal oxide semiconductor (CMOS), or the like.

The second imaging unit 322 has: a second imaging optical system 325 that condenses the second observation light output from the eyepiece optical system 315; and a second imaging element 326 that photoelectrically converts the second observation light condensed by the second imaging optical system 325, and generates the left-eye image signal. The optical axis OP2 of the second imaging optical system 325 is parallel to the optical axis OP1 of the first imaging optical system 323. Configurations of the second imaging optical system 325 and second imaging element 326 are similar to the configurations of the first imaging optical system 323 and first imaging element 324, respectively. The second imaging unit 322 has an imaging area with a size that is the same as that of the imaging area of the first imaging unit 321. The optical zooming mechanism and focusing mechanism that the second imaging optical system 325 has are driven under control by the control device 4.

Figure 3:
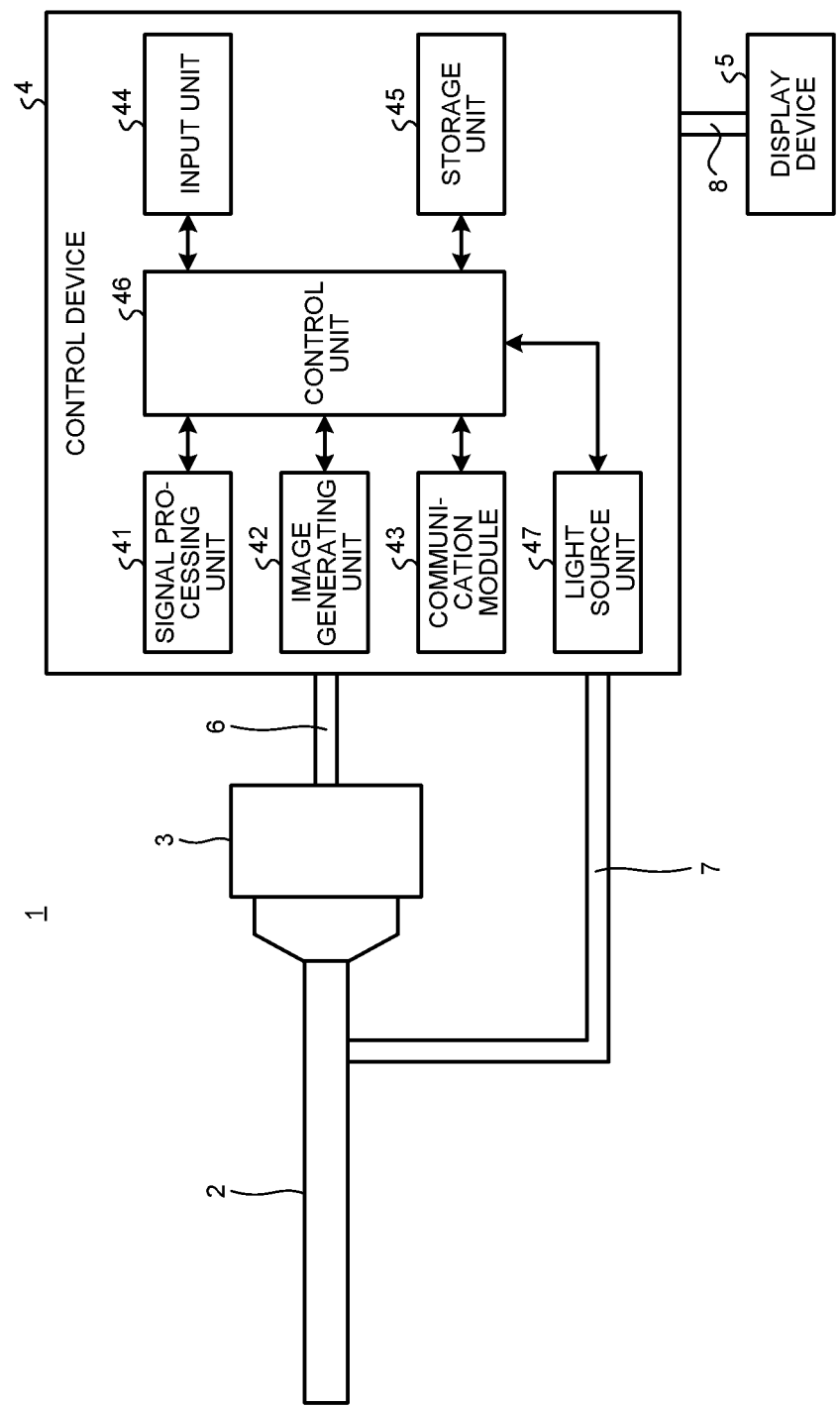
FIG. 3 is a block diagram illustrating a configuration of a control device included in the medical endoscope system according to the embodiment of the present invention.

Described next by reference to FIG. 3 is a configuration of the control device 4. FIG. 3 is a block diagram illustrating the configuration of the control device 4 included in the medical endoscope system 1 according to the embodiment of the present invention. The control device 4 receives the right-eye image signal generated by the first imaging unit 321 and the left-eye image signal generated by the second imaging unit 322, generates a display image signal (a three-dimensional image signal), and outputs the display image signal to the display device 5.

The control device 4 includes a signal processing unit 41, an image generating unit 42, a communication module 43, an input unit 44, a storage unit 45, a control unit 46, and a light source unit 47. The control device 4 may be provided with: a light source unit (not illustrated in the drawings) that generates power source voltage for driving the control device 4 and camera head 3, supplies the power source voltage to each unit of the control device 4, and supplies the power source voltage to the camera head 3 via the transmission cable 6; or the like.

The signal processing unit 41 outputs a digitized imaging signal (a pulse signal) to the image generating unit 42 by performing noise removal and, as necessary, signal processing, such as A/D conversion, on the right-eye image signal and left-eye image signal output by the camera head 3.

Furthermore, the signal processing unit 41 generates synchronization signals and clocks for the camera head 3 and control device 4. A synchronization signal (for example, a synchronization signal for instructing imaging timings for the camera head 3) and a clock (for example, a clock for serial communication) both for the camera head 3 are transmitted to the camera head 3 through a line not illustrated in the drawings, and the camera head 3 is driven based on the synchronization signal and the clock.

The image generating unit 42 performs image processing, such as synchronization processing, white balance (WB) adjustment processing, gain adjustment processing, gamma correction processing, and/or format conversion processing, on the right-eye image signal and left-eye image signal. By using the image-processed right-eye image signal and left-eye image signal, the image generating unit 42 generates the display image signal, which is a three-dimensional image signal corresponding to a display format of the display device 5. The image generating unit 42 generates the three-dimensional image signal by cutting out areas that have been set in the imaging areas of the first imaging unit 321 and second imaging unit 322, and combining the cut-out right-eye image signal and left-eye image signal together.

The image generating unit 42 may generate the three-dimensional image signal by combining the cut-out right-eye image signal and left-eye image signal, which have been up-converted. Specifically, if an image having a size corresponding to a standard definition (SD) image is cut out, the image is up-converted to a high definition (HD) image.

Furthermore, if an image having a size corresponding to an HD image is cut out, the image is up-converted to a 4K image higher in definition. Moreover, if an image having a size corresponding to a 4K image is cut out, the image is up-converted to an 8K image even higher in definition. An SD image is, for example, an image having definition of around 720 in the row direction, and around 480 in the column direction. An HD image is, for example, an image having definition of around 1920 in the row direction, and around 1080 in the column direction. A 4K image is, for example, an image having definition of around 3840 in the row direction, and around 2160 in the column direction. An 8K image is, for example, an image having definition of around 7680 in the row direction, and around 4320 in the column direction.

The communication module 43 outputs signals from the control device 4, to the camera head 3. Furthermore, the communication module 43 receives signals from the camera head 3. That is, the communication module 43 is a relay device, which outputs signals from the respective units of the control device 4 to be output to the camera head 3, and outputs signals input from the camera head 3, to the respective units of the control device 4.

The input unit 44 is a user interface that receives input of various operation signals related to the medical endoscope system 1 including the control device 4. The input unit 44 is realized by use of a user interface such as a keyboard, a mouse, and/or a touch panel.

The storage unit 45 stores therein various programs for operation of the control device 4. These programs include a program for the control device 4 serving as a master to integrally control the medical endoscope system 1. The storage unit 45 is formed by use of: a volatile memory, such as a random access memory (RAM); and a nonvolatile memory, such as a read only memory (ROM).

The control unit 46 controls operation of the medical endoscope system 1 including the control device 4. The control unit 46 integrally controls the medical endoscope system 1 by controlling operation of the signal processing unit 41, image generating unit 42, and light source unit 47, and controlling operation of the camera head 3. The control unit 46 performs light source control by using, for example, brightness information detected from an image.

The light source unit 47 generates illumination light, and supplies the illumination light to the light guide cable 7. The light source unit 47 has: a light source formed by use of a light emitting diode (LED), a halogen lamp, or the like; a light source driver that drives the light source under control by the control unit 46; and an output optical system that condenses light generated by the light source and outputs the light to the light guide.

In the control device 4 having the above functional configuration, the signal processing unit 41, the image generating unit 42, and the control unit 46 are formed by use of: a general purpose processor, such as a central processing unit (CPU); a dedicated integrated circuit that executes specific functions, such as a field programmable gate array (FPGA); or the like.

The display device 5 is, for example, a three-dimensional display of the integral imaging type, multi-lens type, or the like using liquid crystal, organic electroluminescence (EL), or the like, and displays a three-dimensional image based on the three-dimensional image signal generated by the control device 4.

The transmission cable 6 performs communication between the camera head 3 and the control device 4. The transmission cable 6 is a metal cable that transmits therethrough electrical signals. The transmission cable 6 may be a fiber cable that transmits therethrough optical signals. In this case, the camera head 3 may have an electrical-to-optical (E/O) conversion function, and the control device 4 may have an optical-to-electrical conversion function. Furthermore, the transmission cable 6 may be formed by combination of a metal cable and a fiber cable, and may transmit only image signals through optical signals and transmit other signals through electrical signals. Moreover, the communication between the camera head 3 and control device 4 may be performed wirelessly.

The light guide cable 7 is formed of a bundle of plural optical fibers. The light guide cable 7 has one end thereof connected to the control device 4, another end thereof attached to the attachment portion 211 of the rigid endoscope 2, and guide the illumination light generated by the control device 4, to a light guide.

Figure 4:
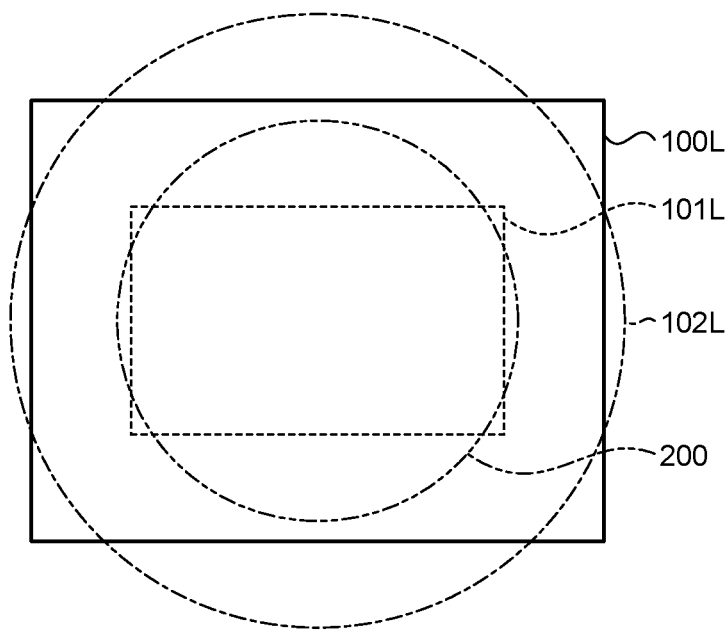
FIG. 4 is a diagram illustrating an image circle of one of optical systems in the rigid endoscope illustrated in FIG. 1, an imaging area of an imaging element that receives light from that optical system, and a cut-out area to be displayed by a display device.

Described next is change in the field of view according to the embodiment by reference to FIG. 4 to FIG. 6. FIG. 4 is a diagram illustrating an image circle of one of optical systems in the rigid endoscope illustrated in FIG. 1, an imaging area of an imaging device that receives light from that optical system, and a cut-out area to be displayed by the display device. FIG. 4 illustrates an image circle of the first condensing optical system 22, and an imaging area of the first imaging unit 321.

An imaging area 100L of the first imaging unit 321 has a cut-out area 101L set therein, the cut-out area 101L corresponding to a size of an image that is able to be displayed by the display device 5. The cut-out area 101L is, for example, rectangular, and is smaller than the imaging area 100L.

An image circle 102L of the first condensing optical system 22 has a size that is able to almost cover the imaging area 100L, and is set so as to be at least larger than a circumcircle circumscribing the cut-out area 101L. Specifically, according to this embodiment, the image circle 102L is a circle having a diameter larger than the long side of the imaging area 100L that is rectangular. The image circle 102L is a circle formed on a plane orthogonal to the optical axis at the focal position, and corresponds to a range, over which light taken in by the first condensing optical system 22 is formed into an image.

Figure 5:
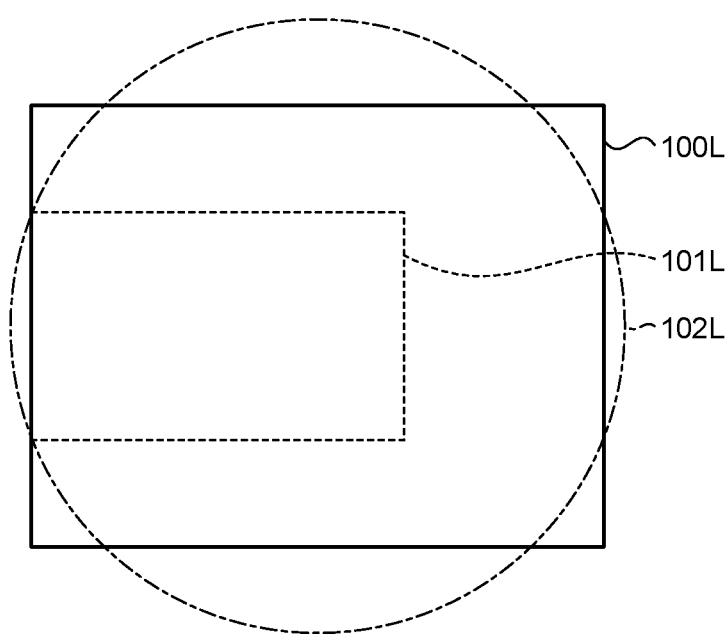
FIG. 5 is a diagram illustrating a case where the cut-out area illustrated in FIG. 4 has been moved.

FIG. 5 is a diagram illustrating a case where the cut-out area illustrated in FIG. 4 has been moved. Since the imaging area 100L is larger than the cut-out area 101L and the image circle 102L is larger than the circumcircle of the cut-out area 101L, the cut-out area 101L is able to be moved within an area where the imaging area 100L and the image circle 102L overlap each other. Specifically, the input unit 44 receives input of instructions corresponding to operation through a mouse or a touch panel, and under control by the control unit 46, the cut-out area 101L is able to be arranged at a position corresponding to the input of the operation. For example, as illustrated in FIG. 5, the cut-out area 101L is able to be moved to a left side from the center (see FIG. 4) of the imaging area 100L.

A cut-out area for a conventional rigid endoscope is designed according to an imaging area. The cut-out area is conventionally set in the same way as the imaging area. For example, if the cut-out area and imaging area are both designed to have the size of the cut-out area 101L, an image circle 200 of the optical system is designed to have a size circumscribing the cut-out area 101L that is rectangular (see FIG. 4). The cut-out area is thus unable to be moved relatively to the imaging area conventionally.

For example, if the angle of view of the cut-out area 101L is 80°, and the angle of view of the imaging area 100L is 120°, the field of view in an image is able to be changed over a range of about 20° at most by movement of the cut-out area 101L. The angle of view referred to herein is an angle formed by joining both end points of a diagonal line of the cut-out area 101L or imaging area 100L to the center of the lens.

Figure 6:
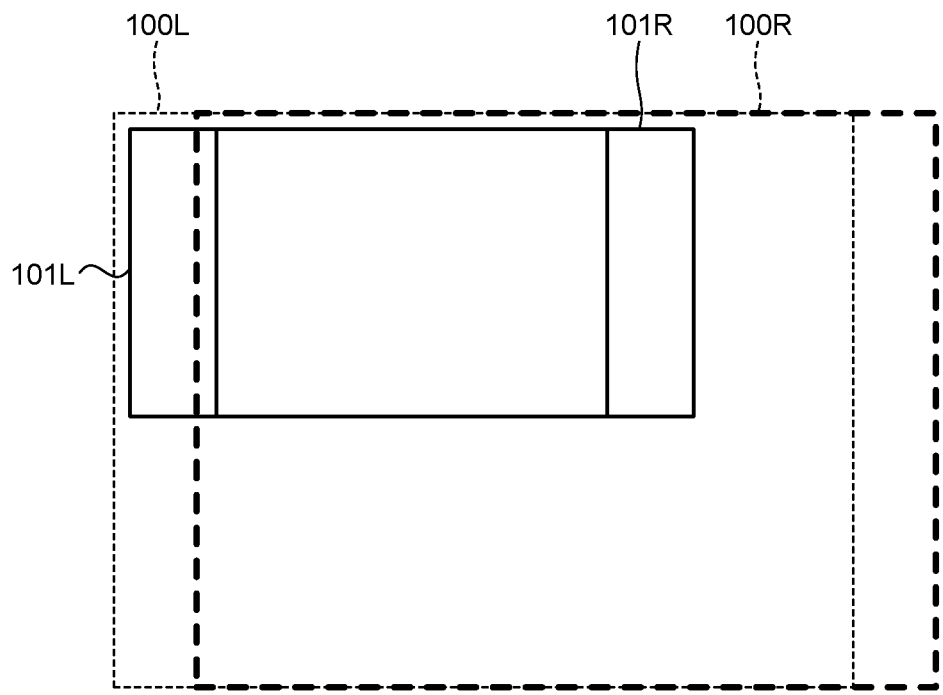
FIG. 6 is a diagram illustrating an imaging area and a cut-out area for a first imaging element, and an imaging area and a cut-out area for a second imaging element.

FIG. 6 is a diagram illustrating an imaging area and a cut-out area for a first imaging device, and an imaging area and a cut-out area for a second imaging device. A cut-out area 101R for the second imaging unit 322 moves, relatively to the imaging area 100R, in the same direction and by the same distance as the cut-out area 101L for the first imaging unit 321. For the generated three-dimensional image to be more natural, the position of the cut-out area may be finely adjusted according to the cut-out position relative to the imaging area. The imaging area and cut-out area for the first imaging element 324 and the imaging area and cut-out area for the second imaging element 326 are at positions, which have been set beforehand, and at which at least parts of their subjects (the cut-out areas) overlap each other and correspond to each other in their imaging areas.

It has been generally known that in an optical system, more distortion is generated toward the outer periphery of the field of view. According to the above described embodiment, since the cut-out area is changed in the imaging area, depending on the cut-out position, a portion may be generated, the portion being where the left eye image and right eye image do not match each other due to the influence of the distortion. If this portion where the left eye image and the right eye image do not match each other is generated, the generated three-dimensional image may create a sense of visual discomfort. According to this embodiment, by correction of the distortion described above, regardless of the position of the cut-out area, a three-dimensional image that does not create a sense of visual discomfort is generated.

Figure 7:
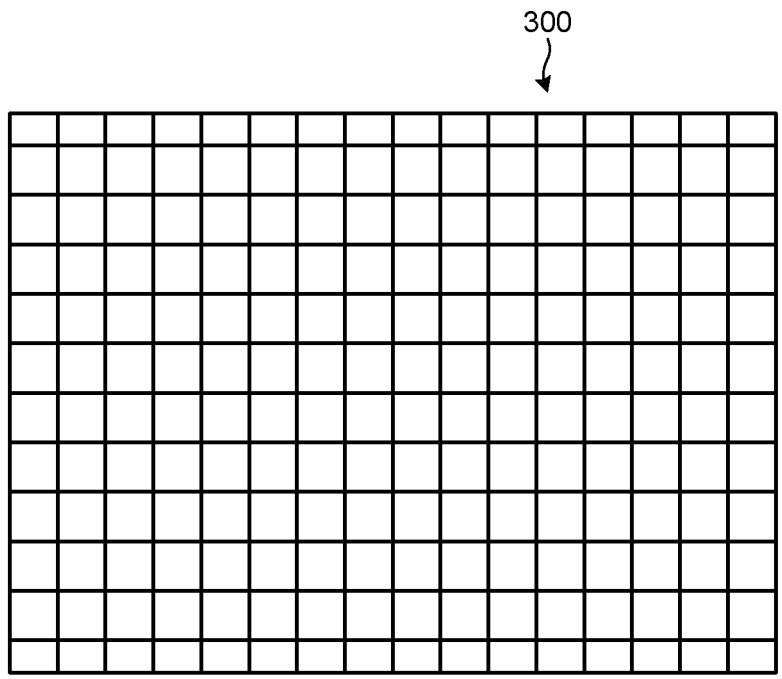
FIG. 7 is a diagram illustrating an example of a subject.
Figure 8:
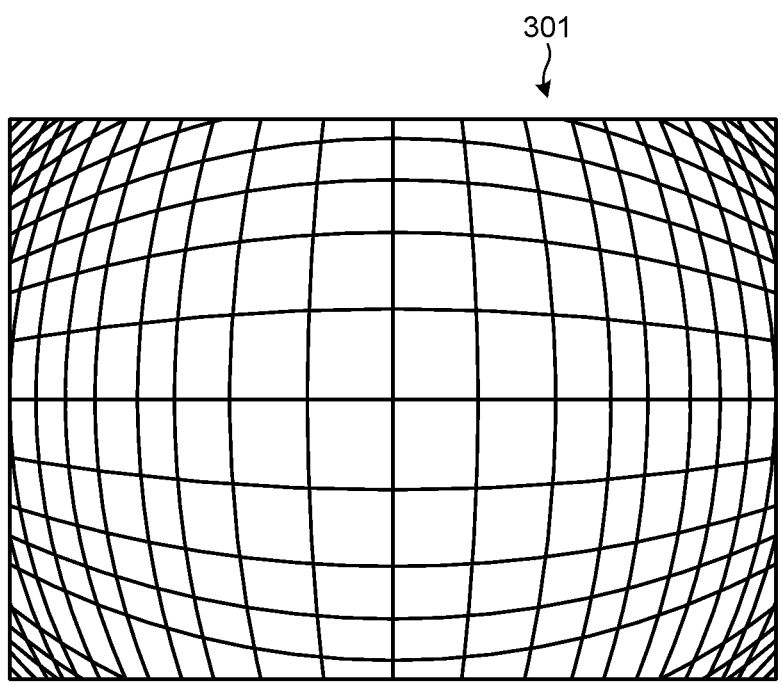
FIG. 8 is a diagram illustrating distortion in imaging of the subject illustrated in FIG. 7.

FIG. 7 is a diagram illustrating an example of a subject. FIG. 8 is a diagram illustrating distortion in imaging of the subject illustrated in FIG. 7. If a subject 300 is planar (see FIG. 7), an image 301 captured via an optical system is, as illustrated in FIG. 8, more distorted toward its outer periphery. For example, if this image 301 corresponds to the imaging areas 100L and 100R described above and the cut-out areas 101L and 101R are set at positions deviated from the center, subject images different from each other are acquired depending on the difference in distortion even if their subjects are the same. When a three-dimensional image is thereby generated, the three-dimensional image creates a sense of visual discomfort.

Figure 9:
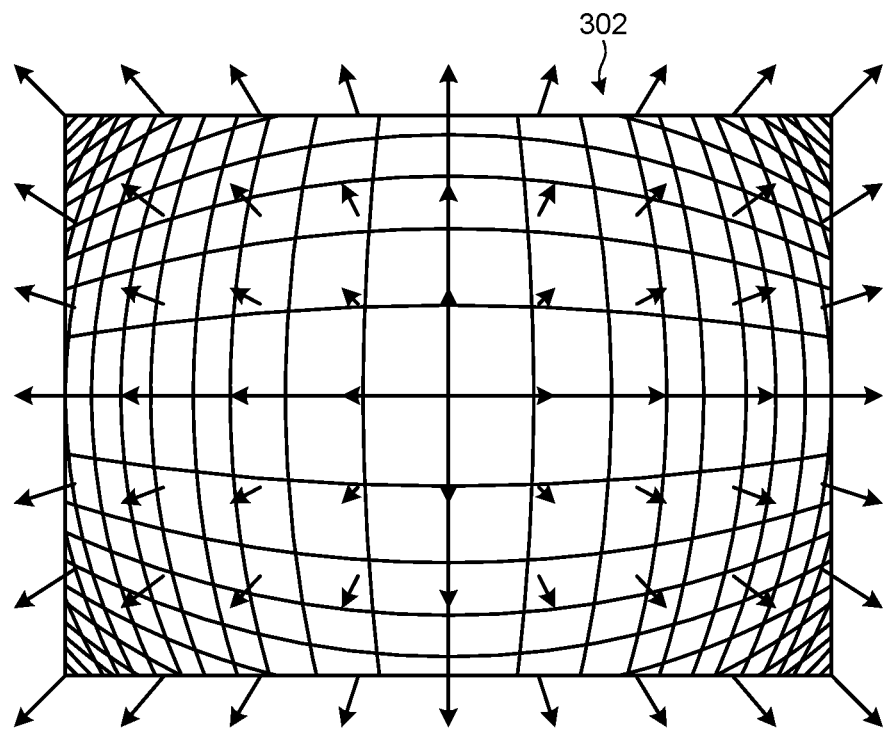
FIG. 9 is a diagram illustrating distortion correction parameters for correction of the distortion illustrated in FIG. 8.

For each location of an imaging area (for example, a pixel position, or a set area formed of plural pixels), a parameter that corrects distortion thereof is thus set beforehand. FIG. 9 is a diagram illustrating distortion correction parameters for correction of the distortion illustrated in FIG. 8. In FIG. 9, the direction of each arrow indicates the direction in which the distortion is corrected, and the length of the arrow indicates the quantity of that correction. By this correcting direction and quantity of correction being set for each location in the imaging area and being stored in the storage unit 45 beforehand, the distortion is able to be corrected. Specifically, the image generating unit 42 acquires the set distortion correction parameters for positions (pixel positions) in the cut-out area by referring to the storage unit 45, and corrects the distortion according the distortion correction parameters for these positions. The left eye image and right eye image are thereby each corrected into a subject 302 on a plane without distortion, and from these left eye image and right eye image, a three dimensional image without a sense of visual discomfort is able to be generated. If no distortion is caused depending on properties of the optical system or correction is not needed, the image generating unit 42 may proceed without the distortion correction described above.

According to the above described embodiment, by generation of a three-dimensional image through change of the position of a cut-out area relative to an imaging area, an image (the three-dimensional image) is acquired without change in the position of the rigid endoscope 2, the image having the position of the subject (field of view) changed therein. In this acquisition, by the positional changes of the cut-out areas relative to the imaging areas being made the same between the first imaging unit 321 and second imaging unit 322, a three-dimensional image having its parallax maintained is generated. As a result, even if the field of view is changed, the hand-eye coordination is able to be maintained. In the above described change in the field of view in the image, only the cut-out position in the imaging area is changed, and the definition is thus maintained.

First Modification

Figure 10:
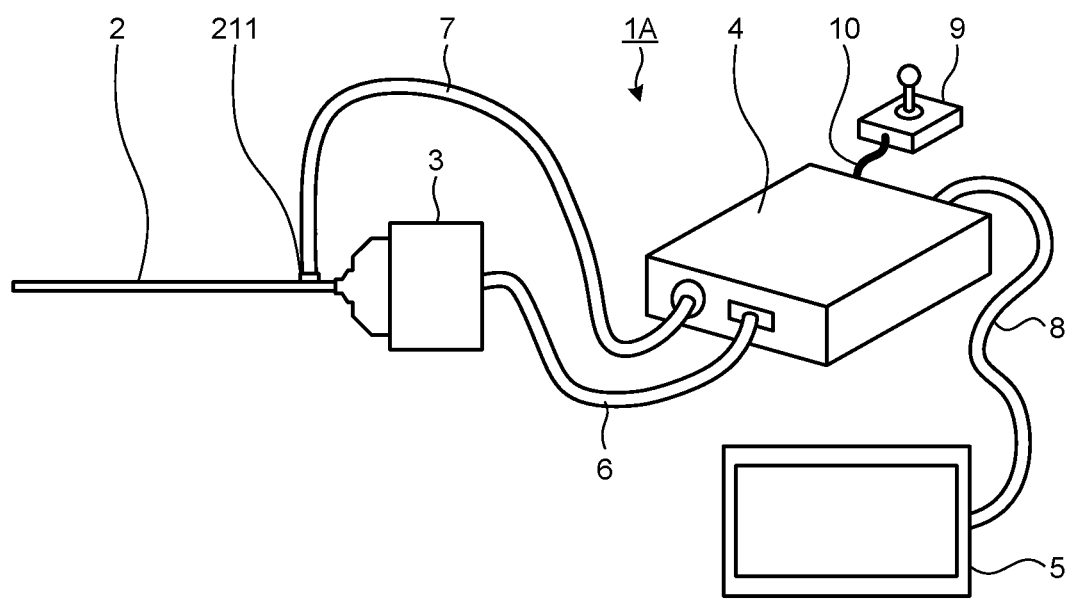
FIG. 10 is a diagram illustrating a schematic configuration of a medical endoscope system according to a first modification of the embodiment of the present invention.

FIG. 10 is a diagram illustrating a schematic configuration of a medical endoscope system 1A according to a first modification of the embodiment of the present invention. According to the above description of the embodiment, input of instructions corresponding to operation of a mouse or a touch panel is received by the input unit 44 and operation of the field of view is controlled by the control unit 46; but according to this first modification, the position of a cut-out area (field of view) is changed by a joystick 9.

The medical endoscope system 1A according to the first modification is a system for stereoscopic observation of the interior of a living body. The medical endoscope system 1A includes: the above described rigid endoscope 2, camera head 3, control device 4, display device 5, transmission cable 6, light guide cable 7, and video cable 8; the joystick 9; and an operation input cable 10 that connects the control device 4 and the joystick 9 to each other, and transmits therethrough an instruction signal for positional change of a cut-out area.

The joystick 9 has a lever that is tiltable in a predetermined direction, and outputs an input signal indicating a tilt direction of the lever.

When the input signal is input via the operation input cable 10, the control unit 46 moves a cut-out area in a direction corresponding to the tilt direction of the lever. In this movement, the control unit 46 moves both the cut-out area for the first imaging unit 321 and the cut-out area for the second imaging unit 322. If no input signal from the joystick 9 is input even when a preset time period elapses, the control unit 46 determines that the movement has been completed, and causes the image generating unit 42 to generate a three-dimensional image by using the left eye image and right eye image of the cut-out areas positioned after the movement.

In this first modification, the quantity of movement and speed of movement of a cut-out area may be changed according to a tilt angle of the joystick 9.

Furthermore, according to the above description of the first modification, the joystick 9 is connected to the control device 4, but the installation position of the joystick 9 is not limited to this example. For example, the joystick 9 may be incorporated in the camera head 3, and be a part of an operating member of the camera head 3.

Second Modification

Figure 11:
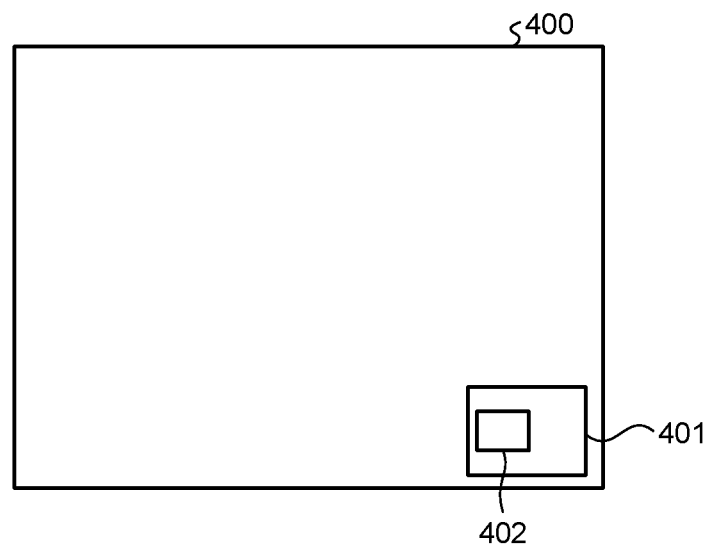
FIG. 11 is a diagram illustrating an example of display by a display device included in a medical endoscope system according to a second modification of the embodiment of the present invention.

FIG. 11 is a diagram illustrating an example of display by a display device included in a medical endoscope system according to a second modification of the embodiment of the present invention. According to this second modification, the display device 5 displays the position of a cut-out area relative to an imaging area. The display device 5 according to this second modification displays, as illustrated in FIG. 11, on a display screen 400 where a three-dimensional image is displayed: an image 401 indicating the imaging area; and an image 402 in the image 401 (imaging area) and indicating a position of the cut-out area for the three-dimensional image currently being displayed on the display screen 400.

According to this second modification, since the position of a cut-out area relative to an imaging area is displayed, the movable direction and quantity of movement are able to be visually recognized by a user upon change in the field of view. The user is thereby able to know the range, over which the field of view is able to be changed.

Third Modification

Figure 12:
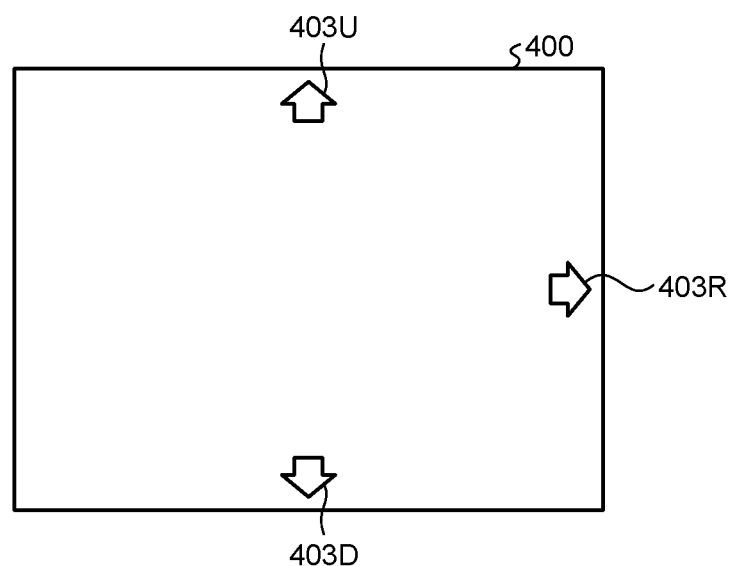
FIG. 12 is a diagram illustrating an example of display by a display device included in a medical endoscope system according to a third modification of the embodiment of the present invention.

FIG. 12 is a diagram illustrating an example of display by a display device included in a medical endoscope system according to a third modification of the embodiment of the present invention. According to this third modification, the display device 5 displays the position of a cut-out area relative to an imaging area. The display device 5 according to this third modification displays, as illustrated in FIG. 12, on the display screen 400 where a three-dimensional image is displayed, arrows 403U, 403D, and 403R indicating directions, in which the field of view is able to be moved. FIG. 12 illustrates that the field of view is movable, on the screen, upward (the arrow 403U), downward (the arrow 403D), and rightward (the arrow 403R). FIG. 12 illustrates the case where the field of view is not movable leftward, but in a case where the field of view is movable leftward, an arrow indicating that the field of view is also movable leftward is displayed.

According to this third modification, since movable directions of a cut-out area relative to an imaging area are displayed on a display screen, the movable directions are able to be visually recognized by a user upon change in the field of view. The user is thereby able to know a range, over which the field of view is able to be changed.

By combination of the first modification with the above described second or third modification, the field of view may be changed even more efficiently by operation of the joystick 9 while the display screen 400 is checked.

Modes for carrying out the present invention have been described thus far, but the present invention should not be limited only to the embodiments described above. According to the above description of the embodiments, the control device 4 performs the signal processing or the like, but the camera head 3 may perform the signal processing or the like instead.

Furthermore, with respect to the above described embodiments, the rigid endoscope 2 having two optical systems has been described as an example, but a single-lens rigid endoscope may be used instead. If a single-lens rigid endoscope is used, for example, only the first condensing optical system is provided, and the imaging unit 32 in the camera head 3 is provided with a single optical path and a single imaging element, too (without the optical path separating unit 31). When a two-dimensional image is generated by such a single-lens rigid endoscope, by change of the position of a cut-out area, the field of view is able to be changed.

INDUSTRIAL APPLICABILITY

As described above, a medical observation device according to the present invention is useful for maintaining the hand-eye coordination and definition even when the field of view is changed.

REFERENCE SIGNS LIST 1, 1A MEDICAL ENDOSCOPE SYSTEM
2 RIGID ENDOSCOPE
3 CAMERA HEAD
4 CONTROL DEVICE
5 DISPLAY DEVICE
9 JOYSTICK
21 INSERTION TUBE
22 FIRST CONDENSING OPTICAL SYSTEM
23 SECOND CONDENSING OPTICAL SYSTEM
31 OPTICAL PATH SEPARATING UNIT
32 IMAGING UNIT
41 SIGNAL PROCESSING UNIT
42 IMAGE GENERATING UNIT
43 COMMUNICATION MODULE
44 INPUT UNIT
45 STORAGE UNIT
46 CONTROL UNIT
311 TRIANGULAR PRISM
312, 313 MIRROR
314, 315 EYEPIECE OPTICAL SYSTEM
321 FIRST IMAGING UNIT
322 SECOND IMAGING UNIT
323 FIRST IMAGING OPTICAL SYSTEM
324 FIRST IMAGING ELEMENT
325 SECOND IMAGING OPTICAL SYSTEM
326 SECOND IMAGING ELEMENT

The invention claimed is:

1. A medical observation device comprising:
a camera to capture an image of a subject, at a first angle of view, the camera including
a first sensor to capture a first image of the subject at the first angle of view, and
a second sensor to capture a second image of the subject at the first angle of view, the second image being offset from the first image; and
circuitry configured to cut, at a second angle of view smaller than the first angle of view, a cut-out region including a region in which the first image and the second image overlap at positions corresponding to each other to form first and second cut-out images smaller than corresponding first and second images, and generate a parallax image based on the first and second cut-out images.

2. The medical observation device according to claim 1, further comprising:
an input configured to receive input of operation for a cut-out position in the image at the first angle of view, wherein
the circuitry is configured to cut, at the second angle of view, the image at the first angle of view, at a position corresponding to the input of the operation received by the input.

3. The medical observation device according to claim 2, wherein the input is a joystick.

4. The medical observation device according to claim 1, wherein the circuitry is configured to perform upconversion and generate the parallax image, after cutting, at the second angle of view, the image at the first angle of view.

5. The medical observation device according to claim 1, wherein the circuitry is further configured to display an entire image area of the subject with an indication of a location of the cut-out images.

6. The medical observation device according to claim 5, wherein the circuitry is further configured to display directions in which a field of view is movable.

7. The medical observation device according to claim 1, wherein the circuitry is further configured to display directions in which a field of view is movable.

8. The medical observation device according to claim 7, wherein the field of view is movable in less than four directions.

9. The medical observation device according to claim 1, wherein the cut-out region is set according to an image size of an image to be displayed.

10. The medical observation device according to claim 1, wherein the cut-out region is smaller than an imaging area of the first and second sensors.

11. The medical observation device according to claim 1, wherein a shape of the cut-out region corresponds to a shape of an image to be displayed.

12. The medical observation device according to claim 1, wherein a shape of the cut-out region is rectangular.

13. A processor for use with a medical observation device including a camera to capture an image of a subject, at a first angle of view, the camera including a first sensor to capture a first image of a subject at the first angle of view, and a second sensor to capture a second image of the subject at the first angle of view, the second image being offset from the first image, the processor comprising
circuitry configured to
cut, at a second angle of view smaller than the first angle of view, a cut-out region including a region in which the first image and the second image overlap at positions corresponding to each other to form first and second cut-out images smaller than corresponding first and second images, and
generate a parallax image based on the first and second cut-out images.

14. The processor according to claim 13, wherein the cut-out region is set according to an image size of an image to be displayed.

15. The processor according to claim 13, wherein the cut-out region is smaller than an imaging area of the first and second sensors.

16. A method, comprising:
capturing a first image of a subject at a first angle of view using a medical observation device;
capturing a second image of the subject at the first angle of view, the second image being offset from the first image using the medical observation device;
cutting, at a second angle of view smaller than the first angle of view, a cut-out region including a region within which the first image and the second image overlap at positions corresponding to each other to form first and second cut-out images smaller than corresponding first and second images; and
generating a parallax image based on the first and second cut-out images.

17. The method according to claim 16, further comprising setting the cut-out region for cutting according to an image size of an image to be displayed.

18. The method according to claim 16, further comprising setting the cut-out region to be smaller than an imaging area of a first sensor that captures the first image and a second sensor that captures the second image.

19. The method according to claim 16, further comprising setting the cut-out region in accordance with a shape of an image to be displayed.

20. The method according to claim 16, further comprising setting the cut-out region to be a rectangle.

* * * * *